United States Patent
Isogai et al.

(10) Patent No.: US 7,650,064 B2
(45) Date of Patent: Jan. 19, 2010

(54) OPHTHALMIC APPARATUS

(75) Inventors: Naoki Isogai, Nishio (JP); Naoto Honda, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 401 days.

(21) Appl. No.: 11/543,814

(22) Filed: Oct. 6, 2006

(65) Prior Publication Data

US 2007/0081128 A1      Apr. 12, 2007

(30) Foreign Application Priority Data

Oct. 11, 2005   (JP) ............................. 2005-297028

(51) Int. Cl.
   *G03B 29/00*   (2006.01)
   *A61B 3/14*   (2006.01)
(52) U.S. Cl. ........................................ 396/18; 351/206
(58) Field of Classification Search .................. 396/18, 396/14; 351/206; 345/650; 348/115
   See application file for complete search history.

(56) References Cited

U.S. PATENT DOCUMENTS 5,463,430 A   10/1995   Isogai et al.
6,304,261 B1 *   10/2001   Shields et al. ............... 715/702
2005/0068497 A1   3/2005   Hanebuchi et al.
2005/0117116 A1 *   6/2005   Murakami ................... 351/211

FOREIGN PATENT DOCUMENTS

JP   A 06-046999   2/1994
JP   A 2004-129711   4/2004
JP   A 2005-103103   4/2005

* cited by examiner

*Primary Examiner*—W. B. Perkey
*Assistant Examiner*—Minh Q Phan
(74) *Attorney, Agent, or Firm*—Oliff & Berridge, PLC

(57) ABSTRACT

An ophthalmic apparatus which is easy to operate. The ophthalmic apparatus includes a measurement unit which measures characteristics of an examinee's eye, an image-pickup optical system for picking up an image of an anterior segment of the eye, a monitor having a screen where the picked-up anterior-segment image is displayed, a plurality of operation switches arranged on the screen or in the vicinity of the screen, a display control part which controls to display function information items indicating functions of the operation switches on the screen, and a changer which makes a selective changeover between a first operation mode in which a state where the function information items are not displayed on the screen is set as a standard state, and a second operation mode in which a state where the function information items are displayed on the screen is set as a standard state.

2 Claims, 4 Drawing Sheets

OPHTHALMIC APPARATUS

BACKGROUND OF THE INVENTION

1. Field of the Invention

The present invention relates to an ophthalmic apparatus for measuring characteristics of an examinee's eye.

2. Description of Related Art

As an ophthalmic apparatus for measuring characteristics of an examinee's eye, there are apparatuses such as an objective eye refractive power measurement apparatus called a refractometer, a corneal shape measurement apparatus called a keratometer, and an intraocular pressure measurement apparatus called a tonometer. These apparatuses are usually provided with a monitor for displaying an image of an anterior segment of the examinee's eye for observation.

In addition, as shown in FIG. 2, for example, some of these apparatuses are provided with a plurality of operation switches arranged in the vicinity of a screen of the monitor, and on the screen, information items explaining functions of the operation switches (hereinafter, function information items) are displayed close to the corresponding operation switches. The operation switches arranged in the vicinity of the screen make it easy to operate and use the apparatus. Additionally, displaying the function information items on the screen allows one operation switch to be provided with a plurality of functions, reducing the number of operation switches. In addition, the operation switches are allowed to be multifunctional.

However, when displayed on the screen, the function information items are superimposed on the image of the anterior segment which is displayed at the same time, which makes the anterior-segment image difficult to see. Meanwhile, when the function information items are displayed smaller so as to make the anterior-segment image easy to see, the function information items become difficult to see, contrarily. In addition, various information items displayed on the screen could give such an impression that the apparatus is complicated and difficult to operate especially to an examiner (operator) who has little experience.

SUMMARY OF THE INVENTION

An object of the invention is to overcome the problems described above and to provide an ophthalmic apparatus which is easy to operate.

To achieve the objects and in accordance with the purpose of the present invention, an ophthalmic apparatus includes a measurement unit which measures characteristics of an examinee's eye, an image-pickup optical system for picking up an image of an anterior segment of the eye, a monitor having a screen where the picked-up anterior-segment image is displayed, a plurality of operation switches arranged on the screen or in the vicinity of the screen, a display control part which controls to display function information items indicating functions of the operation switches on the screen, and a changer which makes a selective changeover between a first operation mode in which a state where the function information items are not displayed on the screen is set as a standard state, and a second operation mode in which a state where the function information items are displayed on the screen is set as a standard state.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
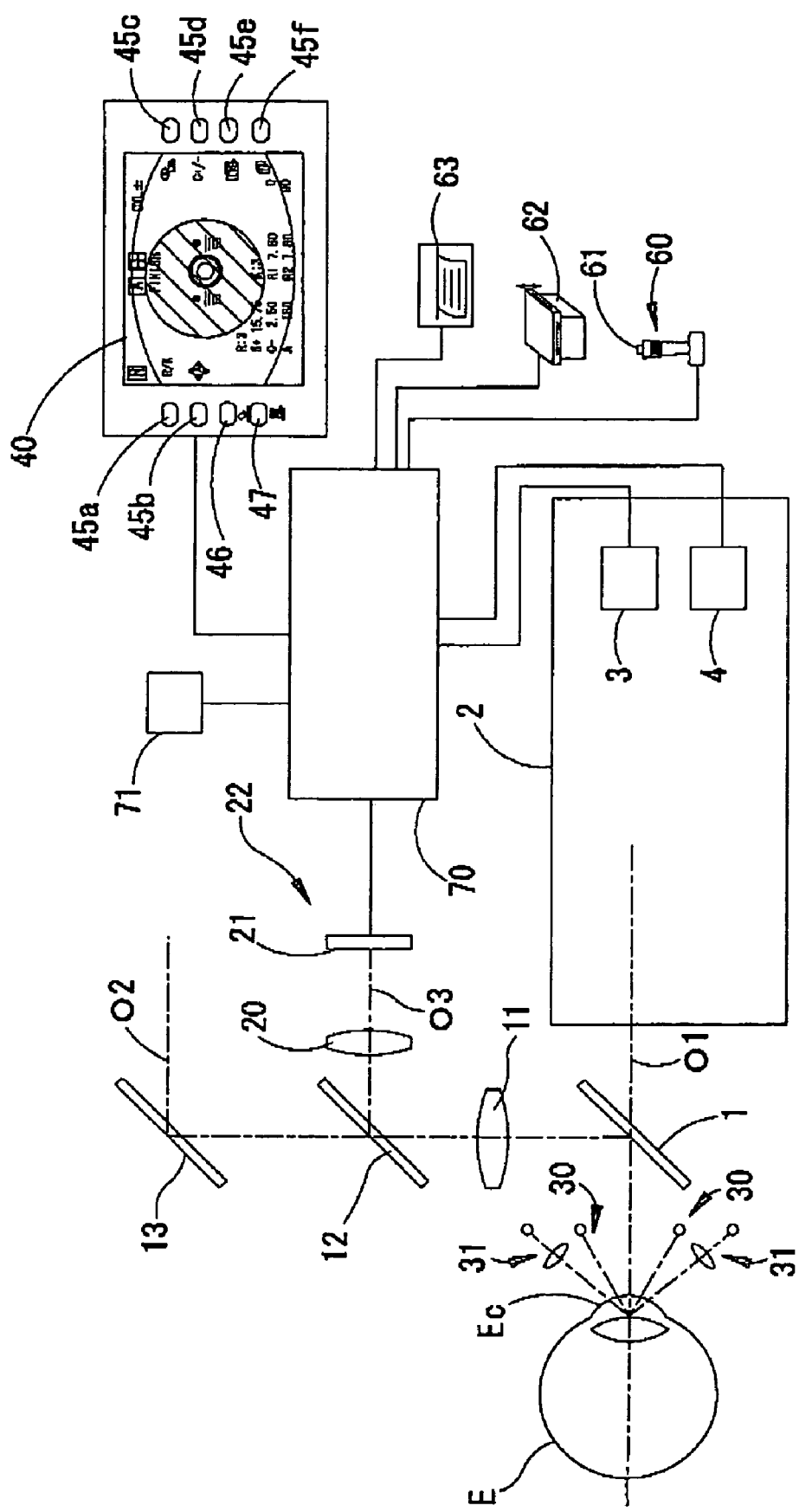
FIG. 1 is a view showing a schematic configuration of an ophthalmic apparatus consistent with the preferred embodiment of the present invention.

A description of one preferred embodiment of an ophthalmic apparatus embodied by the present invention is provided below with reference to the accompanying drawings. FIG. 1 is a view showing a schematic configuration of an ophthalmic apparatus consistent with the preferred embodiment of the present invention. On a transmission optical path O1 of a dichroic mirror 1 arranged in front of an examinee's eye E, arranged is an eye refractive power measurement optical system 2 for measuring eye refractive power being one of characteristics of the eye E. The measurement optical system 2 which includes an infrared light source 3 and a photodetector 4, projects measurement light onto a fundus of the eye E, photo-receives the measurement light reflected from the fundus, and obtains eye refractive power of the eye E based on a photo-receiving result. Regarding the measurement optical system 2, an explanation thereof is omitted since known one can be employed.

On a reflection optical path O2 of the dichroic mirror 1, arranged are an objective lens 11, a dichroic mirror 12, a total reflection mirror 13 and an unillustrated fixation target presenting optical system having a visible light source.

On a reflection optical path O3 of the dichroic mirror 12, arranged is an image-pickup optical system 22 including an image forming lens 20 and a two-dimensional image-pickup element 21 such as an area CCD which is arranged in a position approximately conjugate with the vicinity of an anterior segment of the eye E.

In front of the dichroic mirror 1 (on the part of the eye E with respect to the dichroic mirror 1), arranged are a ring target projection optical system 30 having infrared light sources which projects a ring target for measuring a corneal shape being one of the characteristics of the eye E onto a cornea Ec of the eye E, and an infinite target projection optical system 31 having infrared light sources and collimator lenses which projects infinite targets onto the cornea Ec for detecting an alignment state in a working distance direction with respect to the eye E. Besides, the projection optical system 30 doubles as an illumination optical system which illuminates the anterior segment of the eye E.

The dichroic mirror 1 has a property of transmitting infrared light from the light source 3 of the measurement optical system 2, and reflecting infrared light from the light sources of the projection optical system 30, infrared light from the light sources of the projection optical system 31 and visible light from the light source of the fixation target presenting optical system. The dichroic mirror 12 has a property of transmitting visible light and reflecting infrared light.

A measurement unit includes the measurement optical system 2, the fixation target presenting optical system, the image-pickup optical system 22, the projection optical system 30, the projection optical system 31 and the like, and is moved in a right-and-left direction, an up-and-down direction and a back-and-forth direction (the working distance direction) with respect to the eye E, using a known movement mechanism. The movement mechanism includes a joystick 60 which is used in manual alignment, an electric moving part 62 which is used in automatic alignment, and the like.

An output signal from the photodetector 4 and an output signal from the image-pickup element 21 are input to a calculation and control part 70. Based on the output signals, the calculation and control part 70 obtains eye refractive power and a corneal shape (corneal radius of curvature). In addition, the output signal from the image-pickup element 21 is synthesized with function information items and the like, which are described later, by the calculation and control part 70 and input to a monitor 40. Thus, an anterior-segment image F of the eye E, a ring target image R by the projection optical system 30, and infinite target images M by the projection optical system 31 are displayed on a screen of the monitor 40 (see FIGS. 2 and 3).

The calculation and control part 70 is connected with a memory 71 for storing data on measurement results and the like, the joystick 60, a measurement starting switch 61 mounted at the tip of the joystick 60, the moving part 62, a printer 63, operation switches 45a to 45f (details are described later) arranged in the vicinity of the screen of the monitor 40, a delete switch 46 for inputting an operation signal for deleting the measurement results to the calculation and control part 70, a print switch 47 for inputting an operation signal for printing out the measurement results to the calculation and control part 70, and the like. Besides, the switches 46 and 47 are dedicated switches of which functions are specified, and function information items thereof are respectively illustrated in the vicinity of the switches 46 and 47 (directly underneath the switches 46 and 47 in this embodiment).

Figure 2:
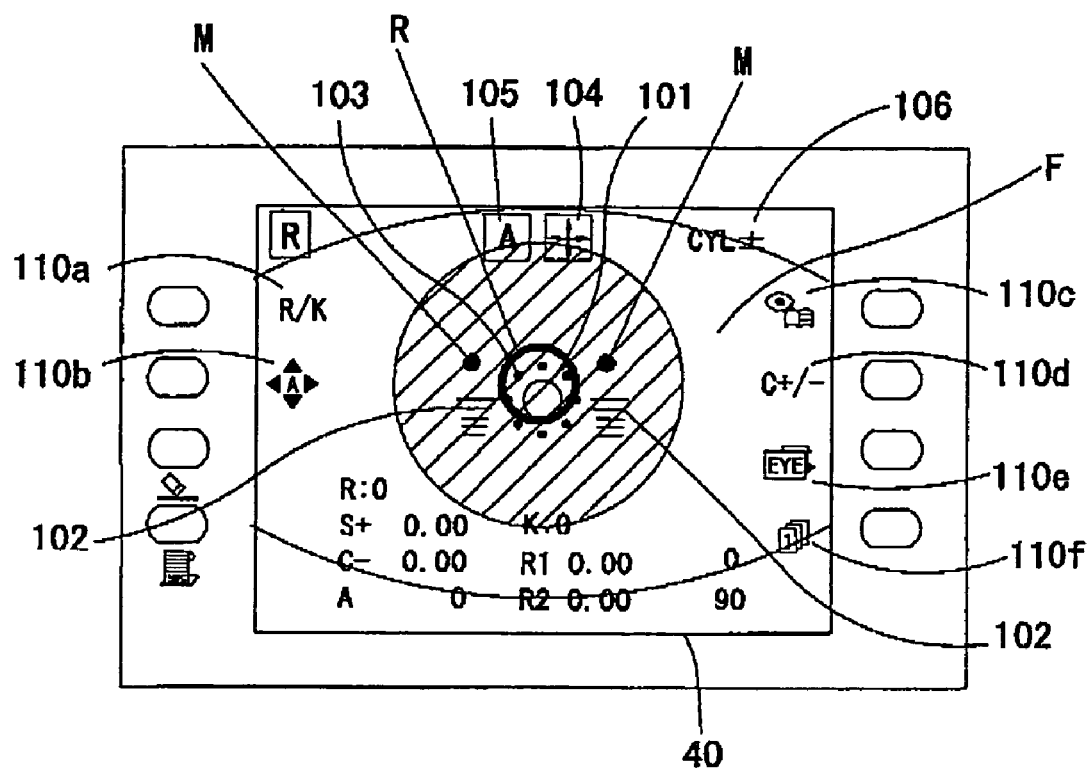
FIG. 2 is a view for illustrating an example of a screen of a monitor in a state where function information items are displayed.
Figure 3:
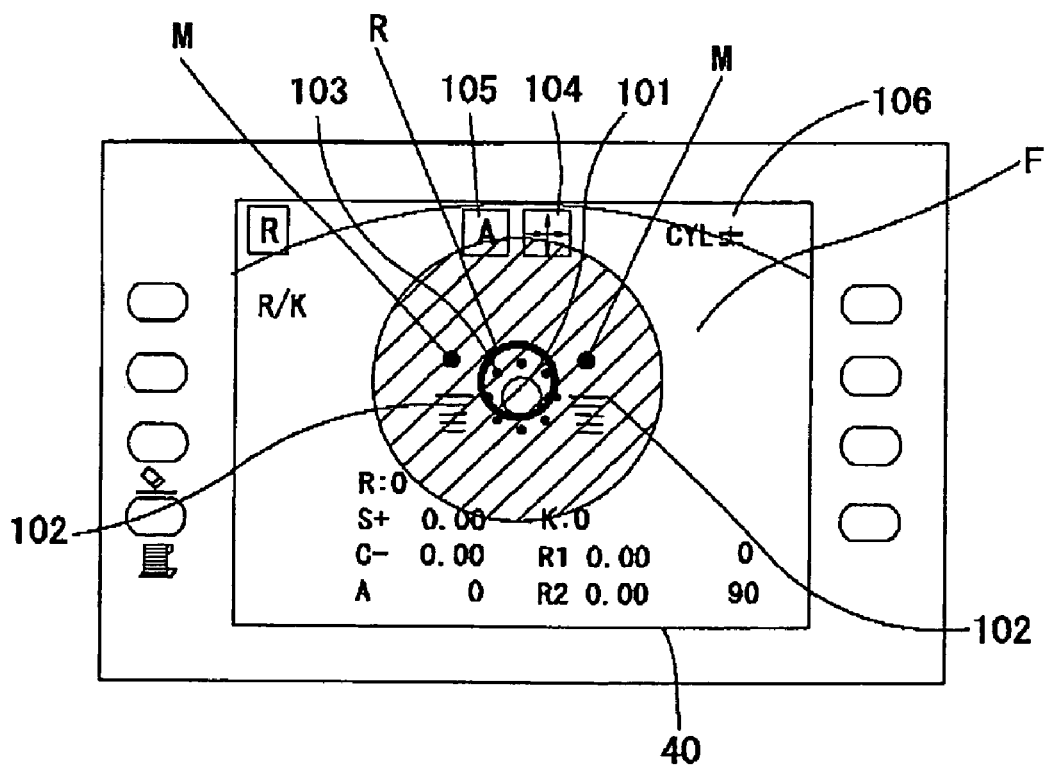
FIG. 3 is a view for illustrating an example of the screen of the monitor in a state where the function information items are not displayed.

The screen of the monitor 40 and the operation switches in the vicinity thereof will be described. As shown in FIGS. 2 and 3, displayed in addition to the anterior-segment image F and the like on the screen of the monitor 40 are a reticle mark 101 used as a reference for alignment in the right-and-left direction and the up-and-down direction of the measurement unit with respect to the eye E, a focusing indicator 102 for indicating an alignment state in the working distance direction of the measurement unit with respect to the eye E, a pupil mark 103 for indicating the measurable minimum pupil diameter, an alignment mode information item 104 which is displayed when an automatic alignment mode is enabled, a measurement mode information item 105 which is displayed when an automatic measurement mode is enabled, a cylinder information item 106 indicating a display style of cylindrical power, measurement results (eye refractive power: "S" is sphere power, "C" is cylinder power and "A" is an astigmatic axial angle, and a corneal shape: "R1" is a corneal radius of curvature in a flattest meridian direction and "R2" is a corneal radius of curvature in a steepest meridian direction), the number of times of measurement ("R" is the number of times of measurement of eye refractive power and "K" is the number of times of measurement of a corneal shape), and the like. Incidentally, "R" at the upper left of the screen of the monitor 40 indicates the eye under measurement, and "R" is displayed when the eye under measurement is a right eye, and "L" is displayed when the eye under measurement is a left eye.

In addition, as shown in FIG. 2, on the far-right and far-left portions of the screen of the monitor 40, function information items 110a to 110f which include letters, signs, drawings and the like indicating functions provided to the operation switches 45a to 45f are displayed close to the corresponding operation switches.

The switch 45a has a function of making a selective changeover among a continuous mode of continuously performing eye refractive power measurement and corneal shape measurement, a single mode of performing eye refractive power measurement, and a single mode of performing corneal shape measurement. The switch 45b has a function of making a selective changeover of the automatic alignment mode between an enabled state and a disabled state, and a selective changeover of the automatic measurement mode between an enabled state and a disabled state. The switch 45c has a function of establishing a comparison mode of comparing the conditions of visibility (for more details, refer to Japanese Patent Application Unexamined Publication No. 2004-129711). The switch 45d has a function of making a selective changeover of the display style of the cylinder power. The switch 45e has a function of printing out an illustrative picture of a refractive state of the eye E based on the measurement results from the printer 63. The switch 45f has a function of shifting the screen of the monitor 40 from an observation screen where the anterior-segment image F and the like are displayed to a screen for setting various parameters such as the number of times of measurement, display styles of the measurement results (measurement values), and printing styles.

Referring to the displayed function information items, an examiner can make setting relating to measurement using the operation switches. For example, when the switch 45a corresponding to the function information item 110a is pushed, the calculation and control part 70 makes the changeover of the mode for measurement based on an operation signal from the switch 45a. In addition, when the switch 45b corresponding to the function information item 110b is pushed, the calculation and control part 70 makes the changeover of the automatic alignment mode between the enabled state and the disabled state, and the changeover of the automatic measurement mode between the enabled state and the disabled state, based on an operation signal from the switch 45b.

In addition, when the switch 45f corresponding to the function information item 110f is pushed, the calculation and control part 70 shifts the screen of the monitor 40 from the observation screen to the parameter setting screen based on an operation signal from the switch 45f. The parameter setting screen is arranged such that a selective changeover is made between a first operation mode in which a state where the function information items are not displayed on the screen of the monitor 40 is set as a standard state, and a second operation mode in which a state where the function information items are displayed on the screen of the monitor 40 is set as a standard state. In the first operation mode, when input of an operation signal from any one of the operation switches is made in the standard state, the function information items are displayed on the screen and subsequent input of operation signals from the operation switches is made enabled while, in the second operation mode, input of operation signals from the operation switches in the standard state is made enabled from the beginning. In other words, in the first operation mode, when input of the operation signal from any one of the operation switches is made in the standard state, the calculation and control part 70 makes a changeover from a screen where the function information items are not displayed (see FIG. 3) to a screen where the function information items are displayed (see FIG. 2).

Besides, if the switch 45f is pushed again, the calculation and control part 70 shifts the screen of the monitor 40 from the parameter setting screen to the observation screen (turns the screen back).

Operations of the apparatus having the above-described configuration will be described. Firstly, a case where the first operation mode is set in the above-described parameter setting is described.

Figure 4:
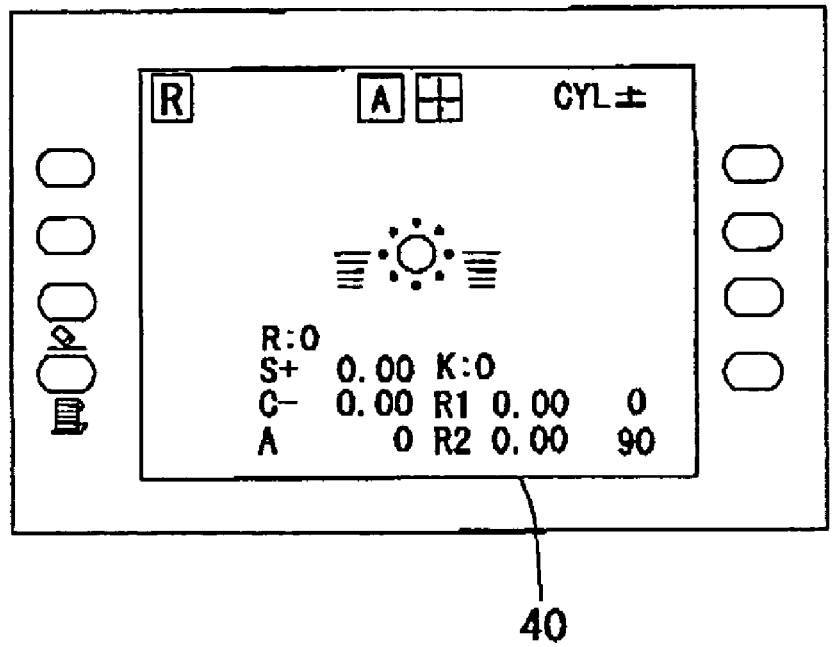
FIG. 4 is a view for illustrating an example of the screen of the monitor immediately after the power is turned on while a first operation mode is set.

In the case where the first operation mode is set, the calculation and control part 70 controls the screen of the monitor 40 to hold the state where the function information items are not displayed (the standard state in the first operation mode) from the moment immediately after the power is turned on (see FIG. 4). When the setting relating to measurement is unnecessary, a face of the examinee is fixed and alignment of the measurement unit with respect to the eye E is performed. Thus, an anterior-segment image of the eye E is picked up by the image-pickup element 21, and the anterior-segment image F and the like are displayed on the screen of the monitor 40 (see FIG. 3).

When the automatic alignment mode and the automatic measurement mode are enabled, the calculation and control part 70 detects an alignment state of the measurement unit with respect to the eye E based on the output signal from the image-pickup element 21. In this case, based on the center position of the detected ring-target image, the calculation and control part 70 obtains an alignment state in the up-and-down and right-and-left directions of the measurement unit with respect to the eye E. In addition, based on a distance between the detected infinite target images and a space in a predetermined meridional direction of the detected ring target image, the calculation and control part 70 obtains an alignment state in the working distance direction of the measurement unit with respect to the eye E (for more details, refer to U.S. Pat. No. 5,463,430 corresponding to Japanese Patent Application Unexamined Publication No. Hei6-46999). Then, based on a result of the detection of the alignment states, the calculation and control part 70 controls and drives the moving part 62 to automatically perform alignment of the measurement unit with respect to the eye E, and upon completion of the alignment, measurement is automatically started.

When the automatic alignment mode and the automatic measurement mode are disabled, the examiner operates the joystick 60 while observing the ring target image R displayed on the screen of the monitor 40, and performs alignment in the up-and-down and right-and-left directions of the measurement unit with respect to the eye E so that the ring target image R and the reticle mark 101 become concentric circles. In addition, the examiner performs alignment in the working operation direction of the measurement unit with respect to the eye E with reference to the focusing indicator 102 (or so that the ring target image R becomes thinnest). Then, upon completion of the alignment, measurement is started by pushing the measurement starting switch 61.

Figure 5:
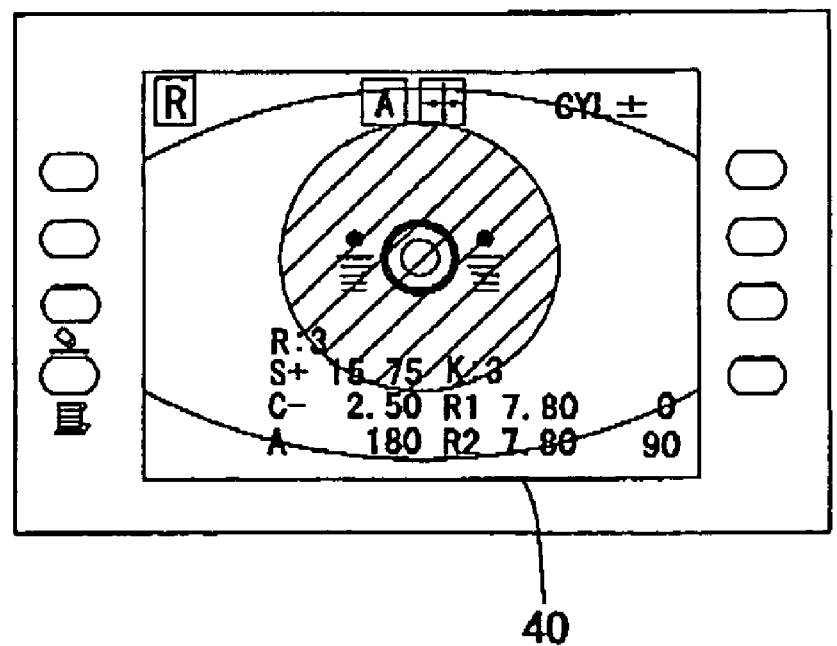
FIG. 5 is a view for illustrating an example of the screen of the monitor in a standard state in the first operation mode at the completion of measurement.

When the continuous mode of continuously performing eye refractive power measurement and corneal shape measurement is set, the calculation and control part 70 firstly calculates a corneal shape (corneal radius of curvature) by analyzing a shape of the detected ring target image. Then, upon completion of the calculation, the calculation and control part 70 controls the monitor 40 to display values of the obtained corneal shape on the screen (see R1 and R2 in FIG. 5). Secondly, the calculation and control part 70 controls to shift to the eye refractive power measurement and controls to light the light source 3 of the measurement optical system 2, and based on the output signal from the photodetector 4, calculates eye refractive power. Then, upon completion of the calculation, the calculation and control part 70 controls the monitor 40 to display values of the obtained eye refractive power on the screen (see S, C and A in FIG. 5).

When making the setting relating to measurement (for example, when making a changeover to the manual alignment mode because the automatic alignment is not achieved properly, or when establishing the comparison mode upon completion of measurement), it is essential only that the examiner pushes any one of the operation switches. When input of an operation signal from any one of the operation switches is made in the standard state, the calculation and control part 70 controls the monitor 40 to display the function information items on the screen and enables subsequent input of operation signals from the operation switches. Thus, the examiner can know the functions of the operation switches referring to the displayed function information items, and also can make the setting relating to measurement.

For example, when the switch 45c is pushed, the calculation and control part 70 controls to establish the comparison mode. In other words, when one operation switch is operated in the state where the function information items are displayed on the screen of the monitor 40, the calculation and control part 70 allows setting relating to measurement in accordance with the previously set function of the operation switch.

When the switch 47 is pushed after the completion of the eye refractive power measurement and the corneal shape measurement, the calculation and control part 70 controls the printer 63 to print out the measurement results.

At this time, in a case where the function information items are displayed on the screen of the monitor 40, the calculation and control part 70 controls the monitor 40 to turn the screen back to the standard state where the function information items are not displayed on the screen of the monitor 40 when the input of the operation signal from the switch 47 is made. Besides, the turning back is made also when the input of the operation signal from the switch 46 is made.

As described above, in the first operation mode, the function information items are not displayed on the screen except when the setting relating to measurement is made; therefore, it becomes easy to grasp a state of the eye E during measurement (including during alignment). In addition, when making the setting relating to measurement, pushing any one of the operation switches allows the function information items to be easily displayed on the screen, which facilitates setting operation. In addition, the state where the function information items are not displayed is brought about in conjunction with the output of the measurement results (or, with the deletion of the measurement results), saving trouble and time to turn the screen back to the state where the function information items are not displayed.

Incidentally, a technique for turning the screen back to the standard state where the function information items are not displayed in the first operation mode may be as follows. Specifically, in a case where the function information items are displayed on the screen of the monitor 40, the calculation and control part 70 controls to turn the screen back to the standard state where the function information items are not displayed when further input of operation signals from the operation switches is not made within a predetermined time after the function information items are displayed. In this case, the time for turning the screen back to the standard state where the function information items are not displayed may be made variably settable. In the case of this technique, however, there is a concern that the examiner might worry (about a breakdown of the apparatus, and the like) since the function information items are made non-displayed during measurement. In addition, when making the setting relating to measurement again after the function information items are made non-displayed, the function information items need to be displayed again, which takes a lot of trouble and time. Hence, the former technique by which the function information items are made non-displayed after the completion of measurement is more preferable.

Hereinafter, a case where the second operation mode is set in the above-described parameter setting will be briefly described. In the case where the second operation mode is set, the calculation and control part 70 controls the screen of the monitor 40 to hold the state where the function information items are displayed (the standard state in the second operation mode) from the moment immediately after the power is turned on. In addition, the calculation and control part 70 enables input of operation signals from the operation switches from the beginning. Thus, the examiner can know the functions of the operation switches referring to the displayed function information items from the moment immediately after the power is turned on, and can make the setting relating to measurement at any time.

The selective changeover between the first operation mode and the second operation mode as described above allows selection as usage or the like. For example, the second operation mode is selected in a case where the setting relating to measurement is made with a high frequency, and the first operation mode is selected in a case where the setting relating to measurement is made with a low frequency, where the state of the eye E during measurement is desired to grasp more in detail, or the like.

Figure 6:
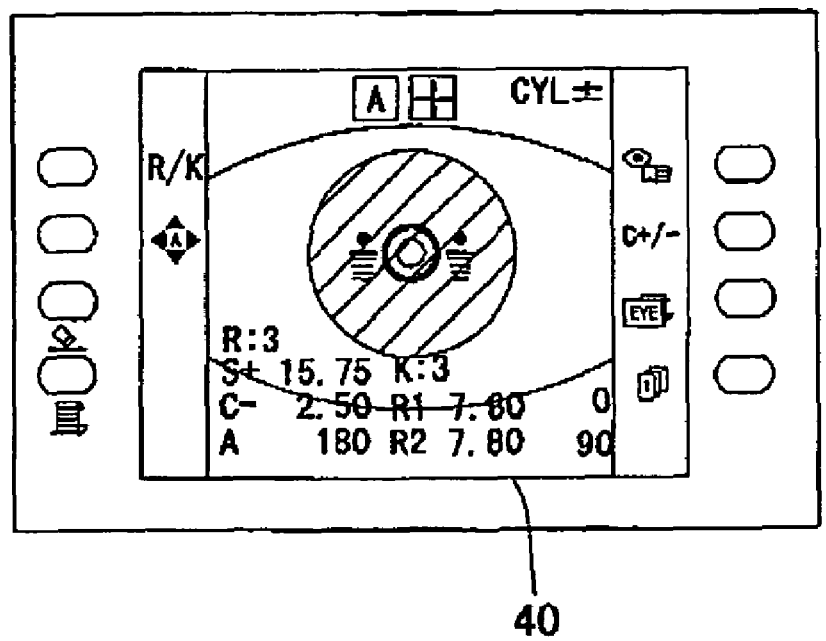
FIG. 6 is a view for illustrating another example of displaying the function information items.

Incidentally, in the above-described embodiment, it is arranged that the function information items are superimposed on the anterior-segment image to be displayed; however, it may be also arranged that the function information items are displayed in a display area provided separately for the function information items, as shown in FIG. 6. In this case, the function information items are displayed without superimposed on the anterior-segment image, which facilitates seeing both of the function information items and the anterior-segment image. Besides, as shown in FIG. 6, if the anterior-segment image is reduced to be displayed, a wide range of the anterior-segment image can be observed even when the function information items are displayed.

In addition, in the first operation mode, it may be arranged that the function information items are reduced to an extent of not interfering with the anterior-segment image and displayed on the screen of the monitor 40 rather than not displayed at all. In this case, when one operation switch is pushed in a state where the reduced function information items are displayed, the calculation and control part 70 controls to enlarge the function information items to be displayed.

Figure 7:
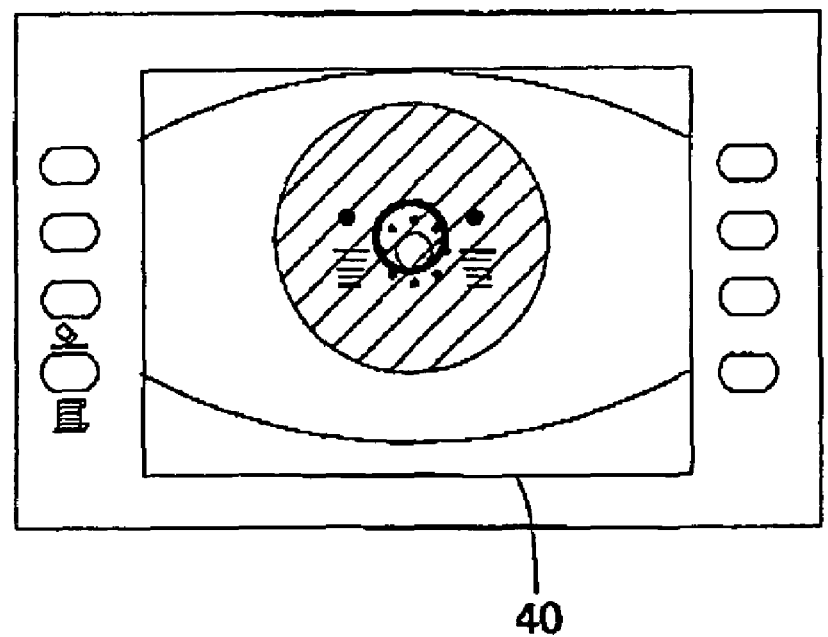
FIG. 7 is a view for illustrating an example of the screen of the monitor in a state where neither measurement results nor measurement conditions are displayed.

In addition, it may be arranged that, in the first operation mode, a state where at least one of the measurement results and the measurement conditions (for example, the alignment mode information item 104, the measurement mode information item 105 and the cylinder information item 106) is not displayed on the screen of the monitor 40 is set as a standard state (see FIG. 7), and in the second operation mode, a state where at least one of the measurement results and the measurement conditions is displayed on the screen of the monitor 40 is set as a standard state. In other words, it may be arranged that a changeover of at least one of the measurement results and the measurement conditions between a displayed state and a non-displayed state is made in response to a changeover of the function information items between a displayed state and a non-displayed state.

In addition, it may be arranged that the operation switches are arranged on the screen of the monitor 40. In other words, it may be arranged that the screen of the monitor 40 has a touch panel function and the function information items in themselves displayed on the screen double as the operation switches (touch switches).

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
 a measurement unit which measures characteristics of an examinee's eye;
 an image-pickup optical system for picking up an image of the examinee's eye to observe the examinee's eye;
 a monitor having a screen where the picked-up image of the examinee's eye is displayed:
 a plurality of operation switches including a plurality of mode changeover switches for making a changeover of a mode for measurement, which are displayed on the screen or arranged in the vicinity of the screen;
 a display control part which controls to display function information items including at least one of letters, signs and drawings indicating functions of the respective mode changeover switches on the screen in relation to the respective mode changeover switches; and
 a selector which makes a selective changeover between:
  a first operation mode in which the function information items are displayed on the screen; and
  a second operation mode in which the function information items are temporarily displayed on the screen based on operation start signals by operation of one of the mode changeover switches, and the function information items are not displayed if there is no operation start signal,
 wherein the display control part controls to display the function information items on the screen based on one of a selection signal of the first operation mode, or a selection signal of the second operation mode and the operation start signals.

2. The ophthalmic apparatus according to claim 1, wherein,
 in the first operation mode, at least one of measurement results obtained by the measurement unit and measurement conditions for the measurement unit is displayed on the screen, and
 in the second operation mode, at least one of the measurement results and the measurement conditions is not displayed on the screen.

* * * * *